United States Patent [19]

James

[11] Patent Number: 4,629,814
[45] Date of Patent: Dec. 16, 1986

[54] PROCESS FOR PREPARING BIS-BROMOALKYL ETHERS

[75] Inventor: Michael P. James, Mont Clare, Pa.

[73] Assignee: Rohm and Haas Company, Philadelphia, Pa.

[21] Appl. No.: 770,032

[22] Filed: Aug. 27, 1985

[51] Int. Cl.[4] ..................... C07C 41/01; C07C 43/02; C07C 43/225
[52] U.S. Cl. .................................. 568/645; 568/647; 568/649; 568/656; 568/663; 568/681; 564/305; 564/487
[58] Field of Search ............... 568/681, 676, 630, 645, 568/647, 649, 656, 663

[56] References Cited

PUBLICATIONS

Sneeden, *J. Chem. Soc.*, 477–478 (1959).
Newman and Chen, 94 *J. Amer. Chem. Soc.*, 2149–2150 (1972).
Keyser, et al., 35 *Tetr. Lett.*, 3263–3264 (1979).
Mamedov and Agaev, 33 *Zh. Obshchei Khim*, 3166–3171 (1963).
Garbers, et al. 43 *Tetr. Lett.*, 3753–3756 (1975).
Clark and Henze, 2 *J. Org. Chem.*, 508–513 (1938).
Blair and Henze, 54 *J. Amer. Chem. Soc.*, 399–401 (1932).
Shorygina, 26 *J. Gen. Chem.*, USSR, 1643–1647 (1956).

*Primary Examiner*—Howard T. Mars
*Attorney, Agent, or Firm*—John C. Demeter

[57] ABSTRACT

This process relates to the preparation of unsubstituted or substituted bis-bromoalkyl ethers by reacting unsubstituted or substituted 1,3-dioxolane or unsubstituted or substituted 1,3-dioxane with thionyl bromide. The bis-bromoalkyl ethers made by this process can be used in preparing biologically active compounds.

5 Claims, No Drawings

PROCESS FOR PREPARING BIS-BROMOALKYL ETHERS

BACKGROUND OF THE INVENTION

This invention relates to an improved process for the preparation of certain bis-bromoalkyl ethers.

It is generally known that lower ($C_1$-$C_4$)bis-bromoalkyl ethers are prepared by reacting a brominated alcohol with an aldehyde and hydrogen bromide to afford the desired bis-bromoalkyl ethers and water. Typically, this reaction gives a yield of from about 75 to 80%. Further purification of the desired product requires separation of water formed during the reaction and then distillation.

It is also known that 1,3-dioxolane can be reacted with acetyl chloride to obtain an "acetate" (chloromethyl acetoxyethyl ether). Further, 1,3-dioxolane can be reacted with $(CH_3)_3$ SiI to obtain a trimethyl silyl ether ($ICH_2$—O—$CH_2CH_2OSi(CH_3)_3$).

These reactions are fundamentally different from the present process in that the second oxygen atom is not removed from the molecule but it is still present in a protected form.

SUMMARY OF THE INVENTION

This invention relates to an improved process for the preparation of bis-bromoalkyl ethers having the formula: $CHR^1Br$—$(CHR^1)_n$—$OCH_2Br$ where n is one or two and each $R^1$ is the same or different hydrogen; ($C_1$-$C_4$)alkyl; or unsubstituted or substituted phenyl having one to three of the same or different halo (chloro, fluoro or bromo), nitro, cyano, ($C_1$-$C_4$)alkyl, ($C_1$-$C_4$)alkoxy, ($C_1$-$C_4$)alkylamino or ($C_1$-$C_4$)dialkylamino having independently the stated number of carbon atoms in each alkyl group which comprises reacting thionyl bromide with unsubstituted or substitituted 1,3-dioxolane or unsubstituted or substituted 1,3-dioxane at about atmospheric pressure at temperatures from about $-10°$ C. to about 70° C. The bis-bromoalkyl ethers made by this process can be used in preparing biologically active compounds.

DETAILED DESCRIPTION OF THE INVENTION

This invention relates to an improved process for the preparation of bis-bromoalkyl ethers. In particular, this invention relates to the preparation of bis-bromoalkyl ethers having the formula $CHR^1Br$—$(CHR^1)_n$—$OCH_2Br$ where n is 1 or 2 and each $R^1$ is the same or different hydrogen ($C_1$-$C_4$)alkyl; or unsubstituted or substituted phenyl having one to three of the same or different halo, nitro, cyano, ($C_1$-$C_4$)alkyl, ($C_1$-$C_4$)alkoxy, ($C_1$-$C_4$)alkylamino or ($C_1$-$C_4$)dialkylamino having independently the stated number of carbon atoms in each alkyl group which comprises reacting thionyl bromide, $SOBr_2$, with unsubstituted or substituted 1,3-dioxolane having the formula

or unsubstituted or substituted 1,3-dioxane having the formula

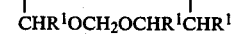

where each $R^1$ is as defined above at about atmospheric pressure at temperatures from about $-10°$ C. to about 70° C.

The 1,3-dioxolane and 1,3-dioxane compounds defined above are commercially available or can be prepared by procedures known in the art.

In the above process, about one mole of thionyl bromide is used for about each mole of 1,3-dioxolane or 1,3-dioxane.

Temperatures utilized for the process of this invention are from about $-10°$ C. to about 70° C., preferably from abut 10° C. to about 30° C.

Typically, yields by weight of from about 90% to about 100% of the bis-bromoalkyl ethers described above are obtained by the process of the present invention. Substantially no by-products are produced by the process of the present invention. The reagents used can be combined in any order.

The bis-bromoalkyl ether prepared by the process of the present invention can be isolated or further reacted to prepare herbicidally active compounds such as certain of the diphenyl ethers disclosed in U.S. Pat. Nos. 3,798,276; 3,928,416; and 4,093,446. Further, the bis-bromoalkyl ethers described above can be used to prepare pharmacologically active compounds such as the penicillin analogs disclosed in U.S. Pat. No. 4,272,437; guanine derivatives such as those disclosed in Elion, et al., *Proc. Nat. Acad. Sci. USA*, 1977, 74, 5716 disclosed as active against Herpes Simplex I, and *Tetr. Lett.*, 1984, 25, 613–616; nucleoside analogs such as thoe described in Keyser, et al., *Tetr. Lett.*, 1979, 35, 3263-3264; and 1,2,4-triazole derivatives such as those disclosed in *Tetr. Lett.* 1984, 25, 611–612. Preparation of such biologically active compounds are by general synthesis routes well known in the art.

The following examples are presented to further illustrate the process of this invention and are not intended to limit the breadth and scope of this invention in any way.

EXAMPLE 1

Preparation of 2-bromoethyl bromomethyl ether 1,3-dioxolane (1 mole) was cooled to 0° C. with stirring. Thionyl bromide (1 mole) was added dropwise over a 30 minute period. The reaction was kept at 0° C. for 2 hours, then allowed to come to room temperature and kept overnight. Moisture was excluded by the use of a drying tube. After 24 hours, the reaction was complete. NMR analysis showed no by-product formation. By weight, the yield of 2-bromoethyl bromomethyl ether was 100%.

EXAMPLE 2

Preparation of 3-bromopropyl bromomethyl ether 1,3-dioxane (2.2 g, 0.025 mol) was cooled to 0° C. with an ice bath. Thionyl bromide (5.2 g, 0.025 mol) was added dropwise with stirring. The reaction was stirred at 0° C. for 1 hour, then allowed to stand at room temperature overnight under nitrogen. The product was obtained in 100% yield as a red liquid. NMR analysis showed the product was greater than 95% pure.

It is to be understood that changes and variations of this process may be made without departing from the spirit and scope of the invention as defined by the appended claims.

I claim:

1. A process for preparing a compound of the formula $CHR^1Br-(CHR^1)_n-OCH_2Br$ where n is one or two and each $R^1$ is the same or different hydrogen; $(C_1-C_4)$alkyl; or unsubstituted or substituted phenyl having one to three of the same or different halo, $(C_1-C_4)$alkyl, or $(C_1-C_4)$alkoxy which comprises:

reacting thionyl bromide with a compound selected from

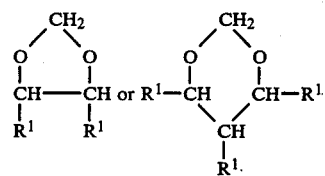

where $R^1$ is as defined above.

2. The process of claim 1 wherein the reaction is carried out at about atmospheric pressure.

3. The process of claim 1 wherein the reaction is carried out at temperatures of from about $-10°$ C. to about $70°$ C.

4. The process of claim 1 wherein the reaction produces substantially no by-products.

5. The process of claim 1 wherein the reaction yields, by weight, from about 90% to about 100% of said compounds.